United States Patent
Rossetto et al.

(10) Patent No.: US 10,058,387 B2
(45) Date of Patent: Aug. 28, 2018

(54) ANTENNA ASSEMBLIES FOR MEDICAL APPLICATIONS

(71) Applicant: COVIDIEN LP, Mansfield, MA (US)

(72) Inventors: Francesca Rossetto, Longmont, CO (US); Joseph D. Brannan, Lyons, CO (US); Joseph A. Paulus, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 84 days.

(21) Appl. No.: 15/191,884

(22) Filed: Jun. 24, 2016

(65) Prior Publication Data

US 2016/0302862 A1 Oct. 20, 2016

Related U.S. Application Data

(63) Continuation of application No. 12/250,171, filed on Oct. 13, 2008, now Pat. No. 9,375,272.

(51) Int. Cl.
| | |
|---|---|
| *A61B 18/18* | (2006.01) |
| *A61B 1/005* | (2006.01) |
| *A61B 17/00* | (2006.01) |
| *A61B 18/00* | (2006.01) |

(52) U.S. Cl.
CPC ........ *A61B 18/1815* (2013.01); *A61B 1/0058* (2013.01); *A61B 2017/00867* (2013.01); *A61B 2018/00077* (2013.01); *A61B 2018/00083* (2013.01); *A61B 2018/00577* (2013.01); *A61B 2018/1853* (2013.01); *A61B 2018/1892* (2013.01); *C08L 2201/12* (2013.01)

(58) Field of Classification Search
CPC ... A61B 18/18; A61B 18/1477; A61B 1/0058; A61B 2017/00867; A61B 2018/00077; A61B 2018/00083; A61B 2018/00577; A61B 2018/1853; A61B 2018/1892; H01Q 13/08; C08L 2201/12
USPC .......................................................... 606/33
See application file for complete search history.

(56) References Cited

U.S. PATENT DOCUMENTS

| | | | |
|---|---|---|---|
| 3,870,977 A | | 3/1975 | Peoples et al. |
| 4,448,198 A | | 5/1984 | Turner |
| 4,632,128 A | | 12/1986 | Paglione et al. |
| 4,712,559 A | * | 12/1987 | Turner .................. H01Q 13/08 607/62 |
| 4,825,880 A | | 5/1989 | Stauffer et al. |

(Continued)

FOREIGN PATENT DOCUMENTS

| | | |
|---|---|---|
| DE | 390937 C | 3/1924 |
| DE | 1099658 B | 2/1961 |

(Continued)

OTHER PUBLICATIONS

European Search Report EP 05002027.0 dated May 12, 2005.

(Continued)

*Primary Examiner* — Manuel Mendez

(57) ABSTRACT

A device for directing energy to a target volume of tissue includes a monopole antenna assembly that includes a monopole antenna radiating section having a monopole antenna element surrounded by a dielectric material. The monopole antenna assembly also includes a ground plane disposed at a proximal end of the monopole antenna radiating section, wherein the ground plane is configured to direct energy into the target volume of tissue.

12 Claims, 9 Drawing Sheets

(56) References Cited

U.S. PATENT DOCUMENTS

| | | | | |
|---|---|---|---|---|
| 5,057,106 | A | * | 10/1991 | Kasevich ............... A61B 18/18 600/549 |
| 5,097,845 | A | | 3/1992 | Fetter et al. |
| 5,190,054 | A | | 3/1993 | Fetter et al. |
| 5,220,927 | A | | 6/1993 | Astrahan et al. |
| 5,246,438 | A | | 9/1993 | Langberg |
| 5,249,585 | A | | 10/1993 | Turner et al. |
| 5,344,435 | A | | 9/1994 | Turner et al. |
| 5,364,336 | A | * | 11/1994 | Carr ...................... A61B 18/18 600/2 |
| 5,370,644 | A | | 12/1994 | Langberg |
| 5,507,743 | A | * | 4/1996 | Edwards ............ A61B 18/1477 600/373 |
| 5,620,480 | A | | 4/1997 | Rudie |
| 5,683,382 | A | | 11/1997 | Lenihan et al. |
| 5,902,251 | A | * | 5/1999 | vanHooydonk ....... A61B 18/18 600/549 |
| 5,921,982 | A | | 7/1999 | Lesh et al. |
| 5,974,343 | A | | 10/1999 | Brevard et al. |
| 6,097,985 | A | | 8/2000 | Kasevich et al. |
| 6,181,970 | B1 | | 1/2001 | Kasevich |
| 6,233,490 | B1 | | 5/2001 | Kasevich |
| 6,325,796 | B1 | * | 12/2001 | Berube ................. A61B 18/18 606/33 |
| 6,364,876 | B1 | | 4/2002 | Erb et al. |
| 6,383,182 | B1 | | 5/2002 | Berube et al. |
| 6,582,426 | B2 | | 6/2003 | Moorman et al. |
| 6,622,731 | B2 | | 9/2003 | Daniel et al. |
| 6,640,139 | B1 | | 10/2003 | Ueberle |
| 6,677,901 | B1 | | 1/2004 | Nalbandian |
| 7,070,597 | B2 | | 7/2006 | Truckai et al. |
| 7,108,696 | B2 | | 9/2006 | Daniel et al. |
| 7,115,126 | B2 | | 10/2006 | Berube et al. |
| 7,118,590 | B1 | | 10/2006 | Cronin |
| 7,276,061 | B2 | | 10/2007 | Schaer et al. |
| 7,387,627 | B2 | | 6/2008 | Erb et al. |
| 7,699,841 | B2 | | 4/2010 | Carr |
| 7,998,139 | B2 | * | 8/2011 | Rossetto ............... A61B 18/18 606/33 |
| 8,068,921 | B2 | | 11/2011 | Prakash et al. |
| 8,343,149 | B2 | | 1/2013 | Rossetto et al. |
| 9,375,272 | B2 | | 6/2016 | Rossetto et al. |
| 2002/0149533 | A1 | | 10/2002 | Toncich |
| 2003/0078573 | A1 | | 4/2003 | Truckai et al. |
| 2004/0044385 | A1 | | 3/2004 | Fenn et al. |
| 2004/0133254 | A1 | | 7/2004 | Sterzer et al. |
| 2006/0116673 | A1 | | 6/2006 | Gauthier et al. |
| 2006/0293651 | A1 | | 12/2006 | Cronin |
| 2007/0161977 | A1 | | 7/2007 | Moorman et al. |
| 2008/0266203 | A1 | | 10/2008 | Rossetto et al. |
| 2009/0054888 | A1 | | 2/2009 | Cronin |

FOREIGN PATENT DOCUMENTS

| | | |
|---|---|---|
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 4303882 A1 | 8/1994 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10328514 B3 | 3/2005 |
| DE | 102004022206 A1 | 12/2005 |
| DE | 202005015147 U1 | 2/2006 |
| EP | 0246350 A1 | 11/1987 |
| EP | 0481685 A1 | 4/1992 |
| EP | 0521264 A2 | 1/1993 |
| EP | 0541930 A1 | 5/1993 |
| EP | 0556705 A1 | 8/1993 |
| EP | 0558429 A1 | 9/1993 |
| EP | 0572131 A1 | 12/1993 |
| EP | 0836868 A2 | 4/1998 |
| EP | 1159926 A2 | 12/2001 |
| EP | 1186274 A2 | 3/2002 |
| EP | 1332724 A1 | 8/2003 |
| FR | 179607 | 11/1906 |
| FR | 1275415 A | 11/1961 |
| FR | 1347865 A | 1/1964 |
| FR | 2235669 A1 | 1/1975 |
| FR | 2276027 A1 | 1/1976 |
| FR | 2313708 A1 | 12/1976 |
| FR | 2502935 A1 | 10/1982 |
| FR | 2517953 A1 | 6/1983 |
| FR | 2573301 A1 | 5/1986 |
| FR | 2862813 A1 | 5/2005 |
| FR | 2864439 A1 | 7/2005 |
| GB | 2434872 A | 8/2007 |
| JP | 55106 | 1/1993 |
| JP | 0540112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | H0928716 A | 2/1997 |
| JP | 11244298 | 9/1999 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| SU | 166452 | 11/1964 |
| SU | 401367 A1 | 10/1973 |
| SU | 727201 A2 | 4/1980 |
| WO | 9505869 A1 | 3/1995 |
| WO | 9956812 A2 | 11/1999 |
| WO | 2004084748 A1 | 10/2004 |

OTHER PUBLICATIONS

European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.

(56) References Cited

OTHER PUBLICATIONS

European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics Figo World Congress 2000, Washington, DC.
MDTECH product literature (Mar. 2000) I'D Wire: product description, 1 page.
MDTECH product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences.cndot.Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Oapril 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl I ):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.825.
S. Humphries Jr. et al., "Finite.cndot.Element Codes to Model Electrical Heating and Non.cndot.Llnear Thermal Transport in Biological Media", Proc. ASME HTD-355, 131 (1997).
Urologix, Inc.—Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—COA-COMP" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.

(56) References Cited

OTHER PUBLICATIONS

Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 09172838.6 dated Dec. 23, 2009.
U.S. Appl. No. 08/483,742, filed Jun. 7, 1995.
U.S. Appl. No. 08/136,098, filed Oct. 14, 1991.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
International Search Report PCT/US98/23950 dated Jan. 14, 1998.
International Search Report PCT/US99/24869 dated Feb. 11, 2000.
European Office Action, Application No. 09 172 838 dated Apr. 14, 2015.
European Search Report dated Oct. 9, 2013 in European Application No. 13004127.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.Tm. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Cosman et al., "Methods of Making Nervous System Lesions" in William RH, Rengachary SS (eds): Neurosurgery, New York: McGraw.cndot.Hill, vol. 111, (1984), pp. 2490-2499.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.

(56) References Cited

OTHER PUBLICATIONS

E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrell et al., "Use of the LigaSure.TM. Vessel Sealing System for Peri-Hilar Vessels in Laparoscopic Nephrectomy" Sales/Product Literature 2000.
Johnson, "Evaluation of the LigaSure.TM. Vessel Sealing System in Hemorrhoidectormy" American College of Surgeons (ACS) Clinic La Congress Poster (2000).
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modem Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
Extended European Search Report from Appl. No. EP 16165913.1 dated Sep. 2, 2016.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
European Examination Report issue in Appl. No. 16 165 913.1 dated Jan. 25, 2018 (5 pages).

* cited by examiner

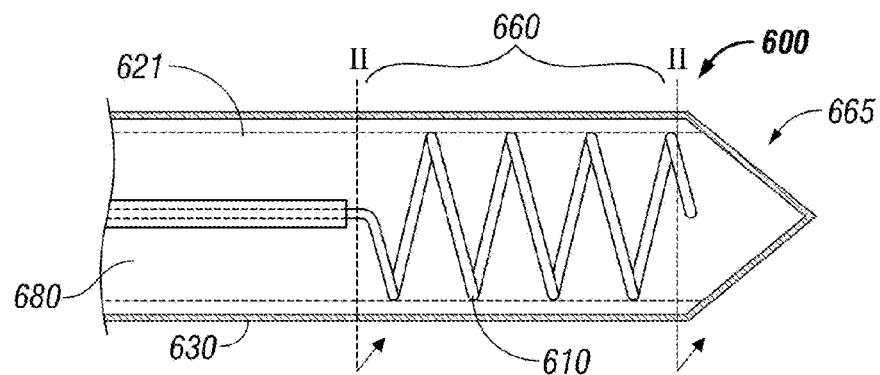
FIG. 6A
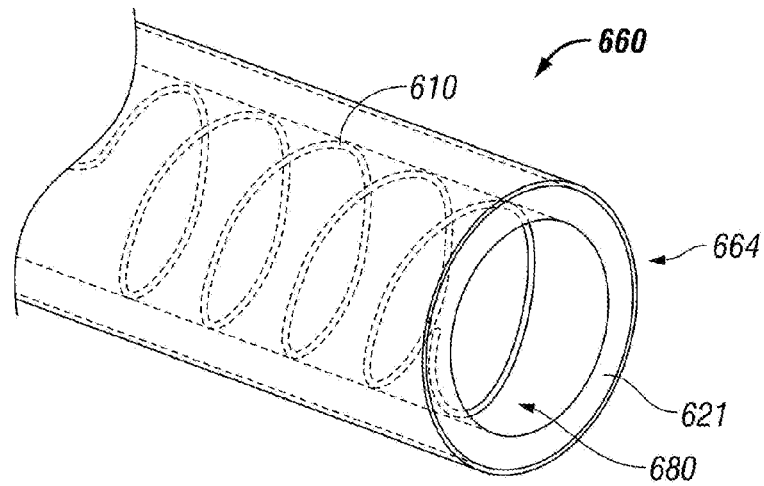
FIG. 6B
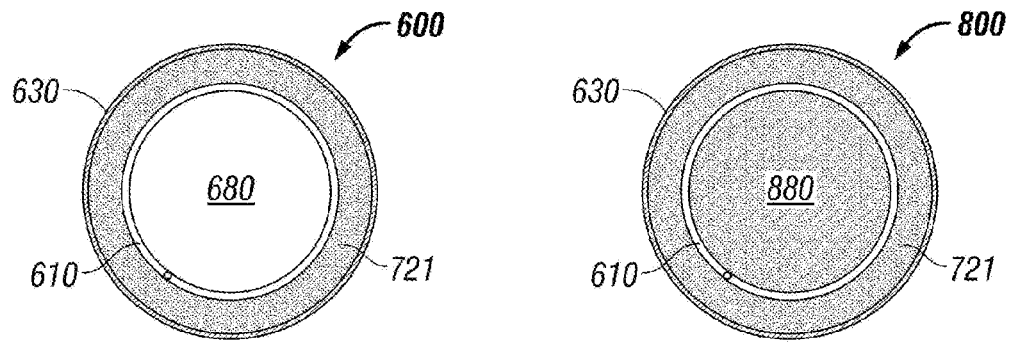
FIG. 7  FIG. 8

ANTENNA ASSEMBLIES FOR MEDICAL APPLICATIONS

CROSS-REFERENCE TO RELATED APPLICATIONS

This application is a continuation application of U.S. patent application Ser. No. 12/250,171, filed Oct. 13, 2008, the entire contents of which are incorporated herein by reference.

BACKGROUND

1. Technical Field

The present disclosure relates to antennas and, more particularly, to electrosurgical devices with antenna assemblies suitable for use in tissue ablation applications.

2. Discussion of Related Art

Treatment of certain diseases requires destruction of malignant tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of cancer cells have been found to denature at elevated temperatures that are slightly lower than temperatures normally injurious to healthy cells. Known treatment methods, such as hyperthermia therapy, use electromagnetic radiation to heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator, which functions as an energy source, and a microwave surgical instrument having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

Microwave energy is typically applied via antenna assemblies that can penetrate tissue. Several types of antenna assemblies are known, such as monopole, dipole and helical. In monopole and dipole antenna assemblies, microwave energy generally radiates perpendicularly away from the axis of the conductor. Helical antenna assemblies have two main modes of operation: normal mode (broadside) and axial mode (endfire). In the normal mode of operation, the field radiated by the helix is maximum in a perpendicular plane to the helix axis. In the axial mode, maximum radiation is along the helix axis.

A typical helical antenna is illustrated in FIG. 1 and includes a conducting wire 100 that is coiled to form a helix having an axis 120 and backed by a conducting ground plane 110. The basic geometrical parameters that define a helical antenna include the diameter D and circumference C of the helix, where $C=\pi D$, the number of turns N of the helix, the center-to-center spacing S between turns, the pitch angle $\alpha$, where $\alpha=\arctan(S/\pi D)$, and the axial length A of the helix, where $A=N \times S$. When the circumference of the helix is small compared with the axial length and the wavelength, the helical antenna radiates in the normal mode (similar to dipole antenna radiation). When the helix circumference is about one wavelength, the helical antenna operates in the axial mode. Typically, a helical antenna radiates in the normal mode when $C<0.4\lambda$ ($\lambda$ is the wavelength) and in the axial mode for approximately $0.75\lambda<C<1.3\lambda$.

During certain procedures, it can be difficult to assess the extent to which microwave energy will radiate into the surrounding tissue, making it difficult to determine the area or volume of the target tissue that will be ablated.

SUMMARY

The present disclosure relates to a device for directing energy to a target volume of tissue including a monopole antenna assembly that includes a monopole antenna radiating section having a monopole antenna element surrounded by a dielectric material. The monopole antenna assembly also includes a ground plane disposed at a proximal end of the monopole antenna radiating section, wherein the ground plane is configured to direct energy into the target volume of tissue.

The present disclosure also relates to a device for directing energy to a target volume of tissue including a ground plane and a number of monopole antenna assemblies N, where N is an integer greater than 1. Each monopole antenna assembly includes a monopole antenna radiating section having a monopole antenna element surrounded by a dielectric material, wherein a proximal end of each monopole antenna radiating section is electrically coupled to the ground plane. The device also includes a power splitter to drive energy into each of the N monopole antenna assemblies, wherein the power splitter is electrically coupled to each monopole antenna element.

Objects and features of the presently disclosed antenna assemblies will become readily apparent to those of ordinary skill in the art when descriptions of embodiments thereof are read with reference to the accompanying drawings.

BRIEF DESCRIPTION OF THE DRAWINGS

FIG. 6A is a schematic diagram of another embodiment of a helical antenna assembly, according to the present disclosure;

FIG. 6B is a perspective view of a portion of the helical antenna assembly shown in FIG. 6A taken along the lines II-II;

FIG. 7 is a cross-sectional view of the helical antenna assembly of FIG. 6B;

FIG. 8 is a cross-sectional view of the helical antenna assembly of FIG. 6B shown with a dielectric material located in an interior of the helical antenna element, according to an embodiment of the present disclosure;

DETAILED DESCRIPTION

Figure 1:
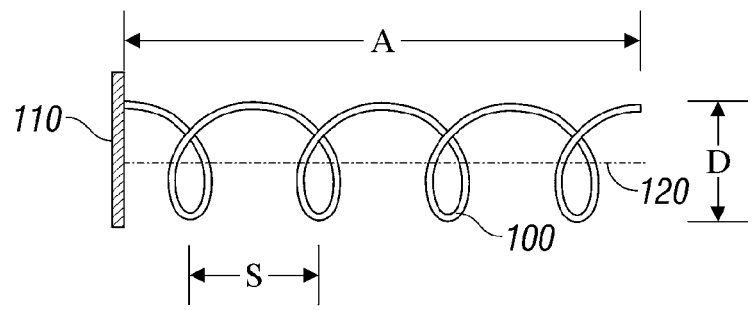
FIG. 1 is a schematic diagram showing the basic geometry of a helical antenna.

Hereinafter, embodiments of the presently disclosed antenna assemblies will be described with reference to the accompanying drawings. Like reference numerals may refer to similar or identical elements throughout the description of the figures.

As used herein, the phrase "ablation procedure" generally refers to any ablation procedure, such as microwave ablation or microwave ablation assisted resection. As used herein, the term "microwave" generally refers to electromagnetic waves in the frequency range of 300 megahertz (MHz) ($3\times10^8$ cycles/second) to 300 gigahertz (GHz) ($3\times10^{11}$ cycles/second). As used herein, the phrase "transmission line" generally refers to any transmission medium that can be used for the propagation of signals from one point to another.

Various embodiments of the present disclosure provide electrosurgical devices for treating tissue and methods of directing electromagnetic radiation to a target volume of tissue. Embodiments may be implemented using electromagnetic radiation at microwave frequencies or at other frequencies. A helical antenna assembly, according to various embodiments, is capable of radiating in axial and normal modes at different stages during the course of a procedure, such as an ablation procedure. Tissue can be ablated around the antenna's radiating section and distal to the radiating section without repositioning the helical antenna assembly. Multiple helical antenna assemblies can be employed in variously arranged configurations. For example, multiple helical antenna assemblies can be placed parallel to each other to substantially simultaneously ablate a target volume of tissue.

Various embodiments of the presently disclosed helical antenna assembly are suitable for microwave ablation and/or for use to pre-coagulate tissue for microwave ablation assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue.

An electrosurgical device including a helical antenna assembly, according to various embodiments, can be used initially in an axial mode to perform ablation distally, and subsequently in a normal mode to perform ablation in areas surrounding the antenna's radiating section. Alternatively, the electrosurgical device can be used initially in a normal mode to perform ablation in areas surrounding the antenna's radiating section, and secondly in an axial mode to ablate in distal areas. It is to be understood that the duration of axial and normal modes of operation and the sequencing of axial and normal modes of operation may be varied depending on the particular application of the helical antenna assembly.

Figure 2:
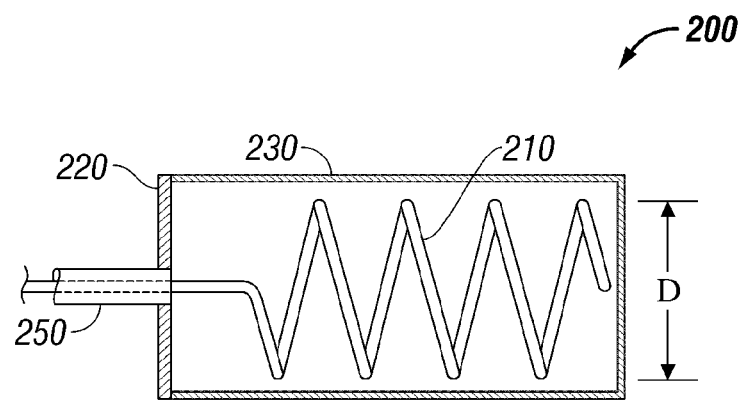
FIG. 2 is a schematic diagram of a helical antenna assembly, according to an embodiment of the present disclosure.
Figure 3:
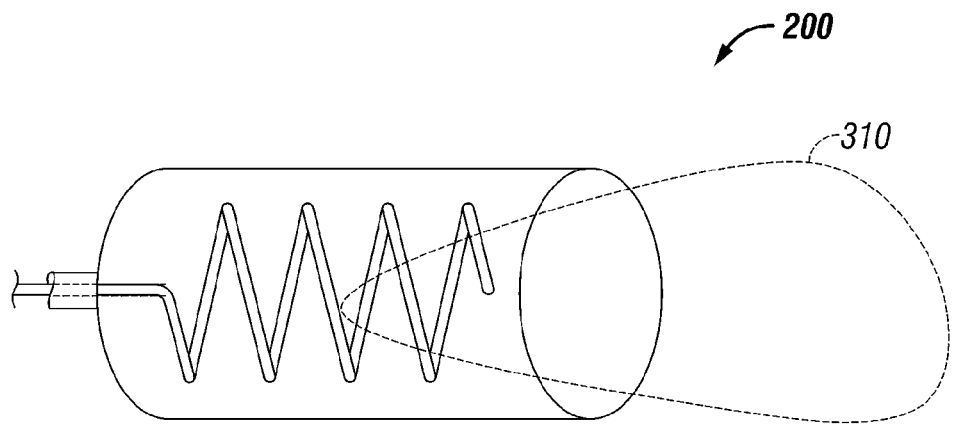
FIG. 3 is a perspective view of the helical antenna assembly illustrated in FIG. 2 showing the transmission pattern in axial mode.

FIGS. 2 and 3 show a helical antenna assembly according to an embodiment of the present disclosure. Referring to FIG. 2, the helical antenna assembly 200 includes a helical antenna element 210, a ground plane 220, a connector 250 that is coupled to the helical antenna element 210, and a housing 230. Helical antenna element 210 can be formed of any suitable material, such as steel, beryllium copper or silver-plated copper. The outer diameter D of the helical antenna element 210 and the number of turns of the helical antenna element 210 may be varied depending on the particular application of the helical antenna assembly. Housing 230 is formed of a dielectric or electrically non-conductive material, such as a non-conductive polymer. Housing 230 may be configured in a variety of shapes and sizes depending on a particular surgical purpose or to accommodate a particular surgical need. Referring to FIG. 3, the helical antenna assembly 200 is shown operating in an axial mode, whereby the transmission pattern 310 radiates outwardly from the distal end of the helical antenna assembly 200.

Figure 4:
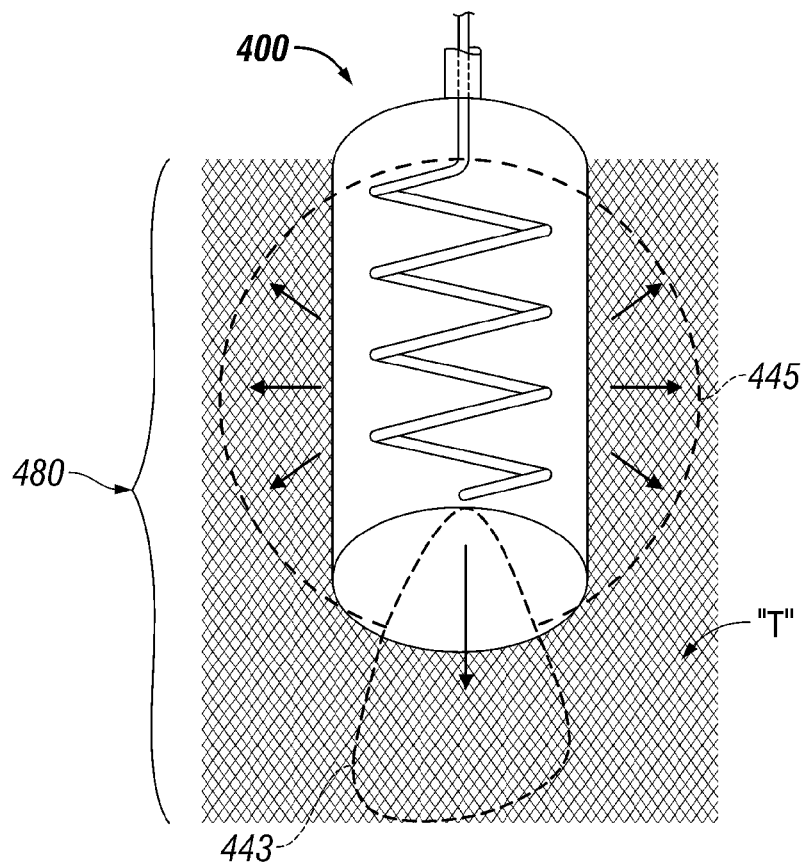
FIG. 4 is a schematic diagram of a helical antenna assembly, according to an embodiment of the present disclosure.

FIG. 4 shows a helical antenna assembly according to another embodiment of the present disclosure. Referring to FIG. 4, the helical antenna assembly 400 is shown positioned for the delivery of electromagnetic energy, such as microwave energy, to the targeted volume 480 of the tissue "T". When the helical antenna assembly 400 radiates in an axial mode, as indicated by the downward arrow, a portion 443 of the tissue "T" is abated distal to the helical antenna radiating section. When the helical antenna assembly 400 radiates in the normal mode, as indicated by the left and right arrows, a portion 445 of the tissue "T" is abated around the helical antenna radiating section. The helical antenna radiating section will be described later in this disclosure with reference to FIGS. 6A and 6B. A dielectric material, e.g., a dielectric gel, may be used between the helical antenna radiating section and the tissue "T" to improve coupling.

Figure 5:
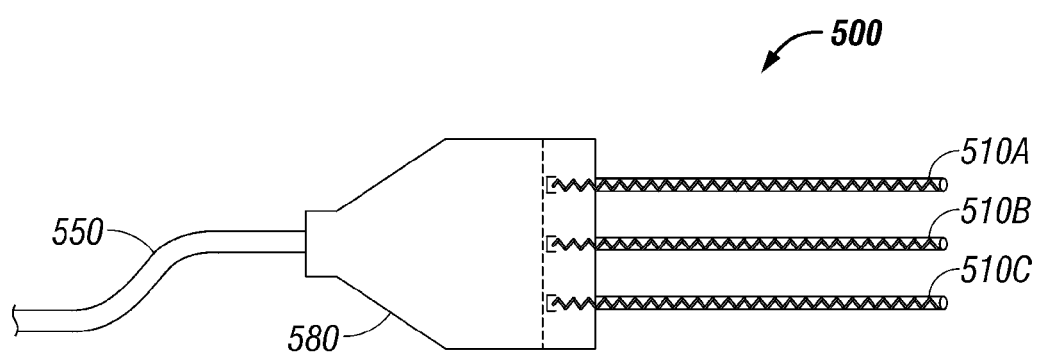
FIG. 5 is a schematic diagram of an electrosurgical device including three helical antenna assemblies, according to an embodiment of the present disclosure.

FIG. 5 shows an electrosurgical device including three helical antenna assemblies according to another embodiment of the present disclosure. The electrosurgical device 500 includes a first helical antenna assembly 510A, a second helical antenna assembly 510B, a third helical antenna assembly 510C, and a housing portion 580 coupled to a transmission line 550. Housing portion 580 may be formed of any suitable material, such as metal or plastic or combination thereof. The shape and size of the housing portion 580 may be varied from the configuration depicted in FIG. 5.

Although first, second and third helical antenna assemblies 510A, 510B and 510C, respectively, extend longitudinally from the distal end of the housing portion 580 and are arranged substantially equally spaced apart and substantially parallel to each other, the number, shape, size and relative spacing of the helical antenna assemblies may be varied from the configuration depicted in FIG. 5. For example, an electrosurgical device may include six helical antenna assemblies, arranged in a two-by-three matrix, or other suitable pattern, to substantially simultaneously ablate a larger target volume of tissue. It is contemplated herein that an electrosurgical device may utilize any number of helical antenna assemblies (or any number of sets of one or more helical antenna assemblies), each helical antenna assembly (or set of helical antenna assemblies) being operable independently or substantially simultaneously with respect to any number of other helical antenna assemblies (or sets of helical antenna assemblies).

First, second and third helical antenna assemblies 510A, 510B and 510C may be axially rigid to allow for tissue penetration. For example, first, second and third helical antenna assemblies 510A, 510B and 510C may be sufficiently small in diameter to be minimally invasive of the body, which may reduce the preparation time of the patient as might be required for more invasive penetration of the body. As shown in FIG. 6A, a helical antenna assembly 600 includes a tip 665, which is advantageously configured to facilitate penetration of tissue. The first, second and third helical antenna assemblies 510A, 510B and 510C may also include tip portions. The helical antenna assemblies 510A, 510B and 510C are inserted directly into tissue, through a lumen, such as, for example, a vein, needle or catheter, placed into the body during surgery by a clinician, or positioned in the body by other suitable methods. The electrosurgical device 500 may include any combination of helical antenna assemblies (e.g., 510A, 510B and 510C) and/or monopole antenna assemblies (e.g., 1920 shown in FIG. 19).

Electrosurgical device 500 may include a power splitter (not shown), disposed within the housing portion 580, to drive energy into each of the first, second and third helical antenna assemblies 510A, 510B and 510C. Transmission line 550 is coupled to an electrosurgical generator (not shown) for generating an output signal. A first frequency $f_1$ is used for axial mode (first wavelength $\lambda_1$) and a second frequency $f_2$ is used for normal mode (second wavelength $\lambda_2$,). For example, $\lambda_2$ may be approximately two to three times larger than $\lambda_1$ and the circumference C of the helix may be in the range of about $0.8\lambda_1$ to about $1.2\lambda_1$ and such that $C<0.4\lambda_2$.

Referring to the embodiment shown in FIG. 6A, the helical antenna assembly 600 includes a helical antenna radiating section 660 and a tip portion 665. Tip portion 665 is advantageously configured for penetrating tissue. Although the surfaces of the tip portion 665 shown in FIG. 6A are generally flat, that surfaces of the tip portion 665 according to various embodiments may be curved or may include a combination of flat, sloped or curved portions. The shape and size of the tip portion 665 may be varied from the configuration depicted in FIG. 6A. The helical antenna radiating section 660 includes a helical antenna element 610, a sleeve member 621 located at the periphery of the helical antenna element 610 coaxially with the helical antenna element 610, and a shell 630 located at the periphery of the sleeve member 621. Helical antenna element 610 may be formed of a shape-memory material, such as copper-zinc-aluminum-nickel, copper-aluminum-nickel and/or nickel-titanium (NiTi) alloys, e.g., to adjust shape of the helical antenna assembly 600 with different temperature perfused fluid.

FIG. 6B shows the helical antenna radiating section 660, which corresponds to the portion of the helical antenna assembly 600 in FIG. 6A taken along the lines II-II. In one embodiment, the sleeve member 621 is formed of a dielectric material and may include a material that has variable dielectric constant, or adjustable dielectric constant, so that effective wavelengths will vary between the axial mode and the normal mode of operation. In one embodiment, the helical antenna radiating section 660 includes a second dielectric material 880 (see FIG. 8) disposed to the interior of the helical antenna element, wherein the sleeve member 621 and the second dielectric material 880 have substantially similar dielectric properties. Sleeve member 621 may be formed of an inflatable element, a shape-memory alloy element, magneto-electrical actuated elements, or other activateable elements to expand the helical antenna radiating section to varied dimensions. Shell 630 encircles the sleeve member 621 and may be formed of a conductive material to improve directionality and to reduce stray electromagnetic radiation emissions. In one embodiment, the shell (1320 shown in FIGS. 13A and 13B) is adapted to be slideably moveable along the periphery of the sleeve member (1360 shown in FIGS. 13A and 13B).

Referring to FIG. 6B, the helical antenna radiating section 660 includes a distal end 664. Helical antenna assembly 600 can be operated in the axial mode to perform a procedure on a first portion of a target volume of tissue, wherein the first portion of the tissue is located distal to end 664 of the helical antenna assembly 600. Helical antenna assembly 600 can be operated in the normal mode to perform a second procedure on a second portion of the target volume of tissue, wherein the second portion is located substantially adjacent to the helical antenna radiating section 660. It is to be understood that various sequences of axial and normal modes of operation may be utilized depending on the particular application of the helical antenna assembly 600.

FIG. 7 is a cross-sectional view of the helical antenna assembly of FIG. 6B. FIG. 7 shows the helical antenna assembly 600 including the helical antenna element 610 enclosed by a first dielectric material 721, and the shell 630 which surrounds the length of the first dielectric material 721. First dielectric material 721 may include ferroelectric dielectric materials, which through applied DC voltage may allow control of the depth and spread of the power deposition pattern. Shell 630 may be formed of an electrically conductive material, e.g., metal, and may be used as the charge accumulation conductor generating the DC field, with the helix being the opposite electrode. Located to the interior of the helical antenna element 610 is a cavity 680. As described hereinbelow, interior cavity 680 may include a dielectric material disposed therein.

FIG. 8 is a cross-sectional view of the helical antenna assembly of FIG. 6B shown with a dielectric material disposed to the interior of the helical antenna element, according to an embodiment of the present disclosure. The antenna assembly 800 of FIG. 8 is similar to the helical antenna assembly 600 shown in FIG. 7, except that the helical antenna assembly 800 includes a second dielectric material 880 disposed to the interior of the helical antenna element 610, i.e., instead of the interior cavity 680. In one embodiment of helical antenna assembly 800, the first dielectric material 721 and the second dielectric material 880 have substantially similar dielectric properties. In other embodiments, the dielectric properties may be substantially higher or lower in $\varepsilon_r'$, $\varepsilon_r''$. Second dielectric material 880 may include ferroelectric dielectric materials. Enclosing the helical antenna element 610 and the dielectric load, e.g., first and second dielectric materials 721 and 880, with conductive shell 630 may aid directionality of the helical antenna assembly 800. Shell 630 may be longitudinally divided into a plurality of electrodes with a dielectric material disposed between the electrodes, for beam steering, e.g., through ferroelectric manipulation.

Figure 9A:
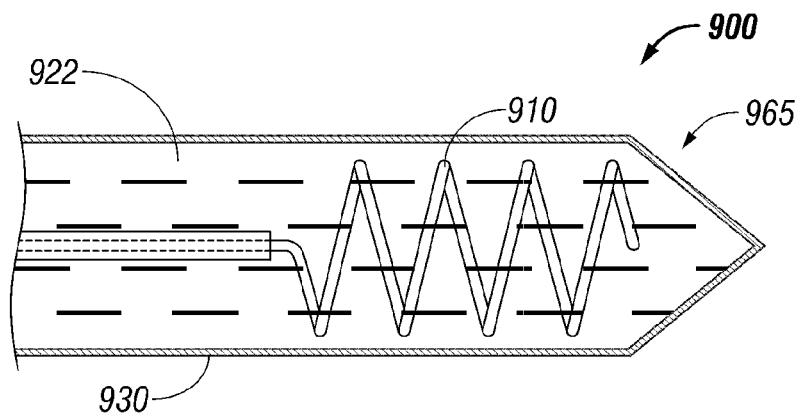
FIG. 9A is a schematic diagram of another embodiment of a helical antenna assembly, according to the present disclosure.
Figure 9B:
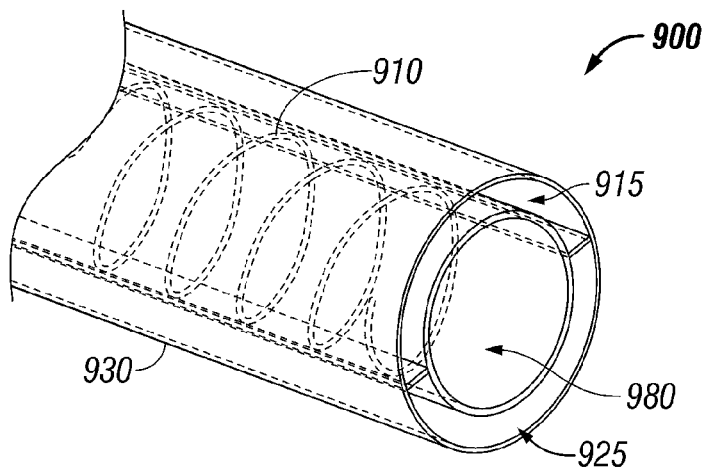
FIG. 9B is a perspective view of a portion of the helical antenna assembly shown in FIG. 9A.

FIGS. 9A and 9B show a helical antenna assembly according to another embodiment of the present disclosure, wherein the helical antenna assembly 900 includes a helical antenna element 910, a fluid 922, an outer shell 930, and a tip 965. Tip 965 is advantageously configured to facilitate penetration of tissue. Helical antenna assembly 900 also includes an inner shell, located at the periphery of the helical antenna element 910 and surrounding the length of the helical antenna element 910, and two longitudinally formed partitions, which form a first channel 915 and a second channel 925 in the space between the outer shell 930 and the periphery of the helical antenna element 910. Each of the first and second channels 915, 925 are utilized to hold the fluid 922. In one embodiment, each of the longitudinally formed partitions include a number of openings formed therein for placing the first and second channels 915, 925 in fluid communication. In the embodiment illustrated in FIG. 9B, the first and second channels 915 and 925 have substantially equal dimensions. Although two channels are shown in FIG. 9B, the helical antenna assembly 900 may include a single channel or multiple channels.

Figure 10:
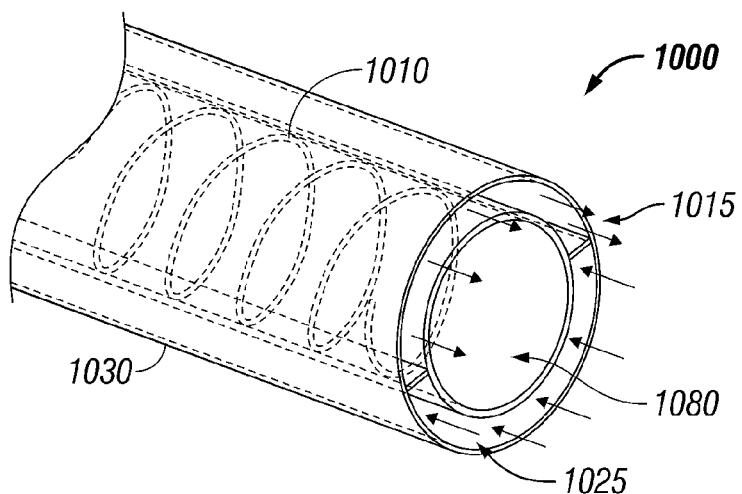
FIG. 10 is a perspective view of the helical antenna assembly of FIG. 9B shown with a circulating fluid, according to an embodiment of the present disclosure.

FIG. 10 shows a helical antenna assembly according to yet another embodiment of the present disclosure, wherein the helical antenna assembly 1000 includes a helical antenna element 1010 and an outer shell 1030. The helical antenna assembly 1000 also includes a first channel 1015 and a second channel 1025, which are similar to the first and second channels 915, 925 shown in FIG. 9B, except that the distal end portions of the first and second channels 1015, 1025 are adapted to allow fluid circulation in opposing directions, as indicated by the right and left arrows. Fluids having different dielectric constants ε are circulated around the helical antenna radiating section, and the effective wavelength changes depending on the fluid dielectric properties.

The relationship between the circumference C of the helical antenna element 1010 and the effective wavelength λ can be expressed by the equation I=C/(f×sqrt(ε)), where frequency f=1/λ. For example, in cases when the dielectric constant $\varepsilon_1$ of a first fluid is in the range of about three to nine times the dielectric constant $\varepsilon_2$ of a second fluid, $0.8\lambda_1 < C < 1.2\lambda_1$ and $C < 0.4\lambda_2$. In one embodiment wherein fluids are circulated around the helical antenna radiating section, and wherein helical antenna element 1010 is formed of a shape memory alloy, the fluid temperature is varied to change the shape of the helical antenna assembly 1100, for example, to assist with altering normal versus endfire mode.

Figure 11A:
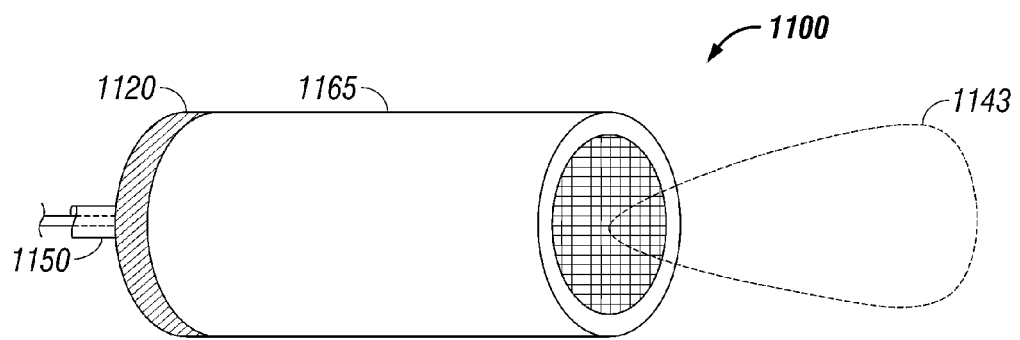
FIG. 11A is a schematic diagram of yet another embodiment of a helical antenna assembly, according to the present disclosure.
Figure 11B:
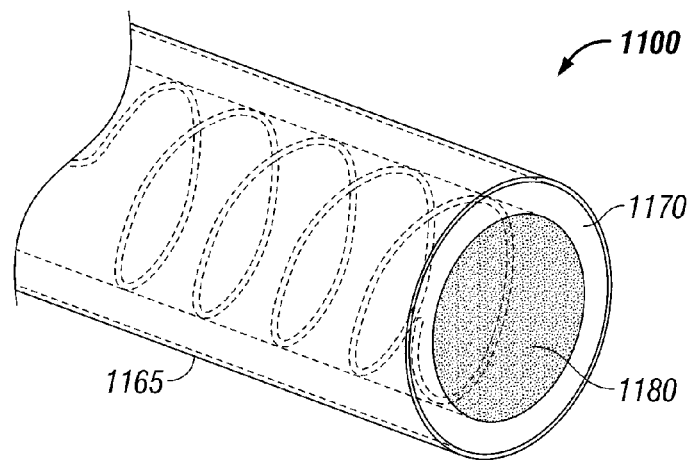
FIG. 11B is a perspective view of a portion of the helical antenna assembly shown in FIG. 11A.

FIGS. 11A and 11B show a helical antenna assembly 1100 that includes a housing 1165, a helical antenna element disposed with the housing 1165 and backed by a conducting ground plane 1120, and a connector 1150 which is coupled to the helical antenna element. Helical antenna assembly 1100 is shown operating in an axial mode, whereby the transmission pattern 1143 extends outwardly from the distal end of the helical antenna assembly 1100. Referring to FIG. 11B, the helical antenna assembly 1100 also includes a dielectric element 1180 and a cavity 1170 defined between the outer shell of the housing 1165 and the periphery of the dielectric element 1180. Cavity 1170 includes channels for holding a fluid, e.g., first and second channels 915 and 925 for holding fluid 922 as shown in FIG. 9B.

Figure 12:
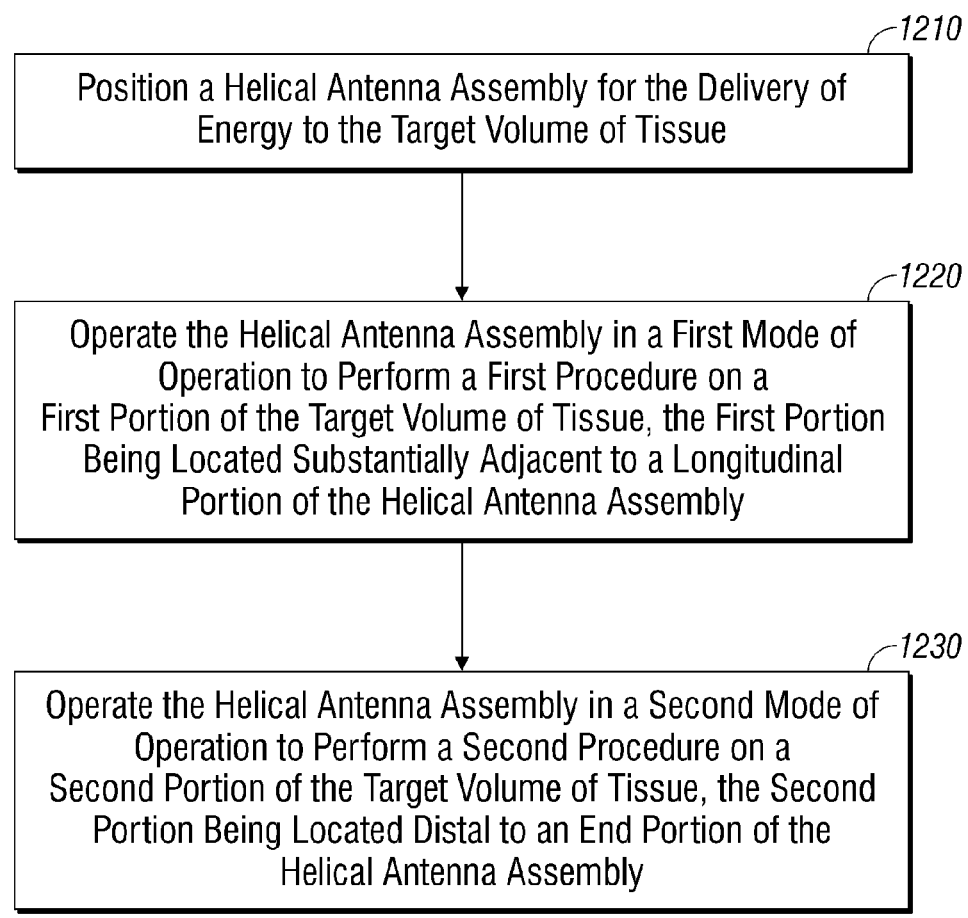
FIG. 12 is a flowchart illustrating a method for directing energy to a target volume of tissue, according to an embodiment of the present disclosure.

FIG. 12 is a flowchart illustrating a method for directing energy to a target volume of tissue, according to an embodiment of the present disclosure. In step 1210, a helical antenna assembly, e.g., 400, is positioned for the delivery of energy to the target volume of tissue. The helical antenna assembly 400 may be inserted directly into tissue (e.g., as shown in FIG. 4), inserted through a lumen, e.g., a vein, needle or catheter, placed into the body during surgery by a clinician, or positioned in the body by other suitable methods.

In step 1220, the helical antenna assembly is operated in a first mode (e.g., a normal mode) of operation to perform a first procedure on a first portion of the target volume of tissue, the first portion being located substantially adjacent to a longitudinal portion of the helical antenna assembly.

In step 1230, the helical antenna assembly is operated in a second mode (e.g., an axial mode) of operation to perform a second procedure on a second portion of the target volume of tissue, the second portion being located distal to an end portion of the helical antenna assembly.

Figure 13A:
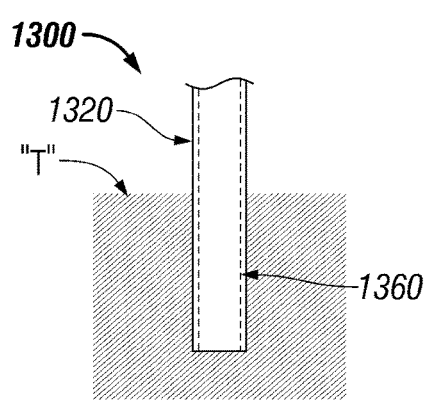
FIGS. 13A and 13B are schematic diagrams of a helical antenna assembly including a moveable shell, according to an embodiment of the present disclosure.
Figure 13B:
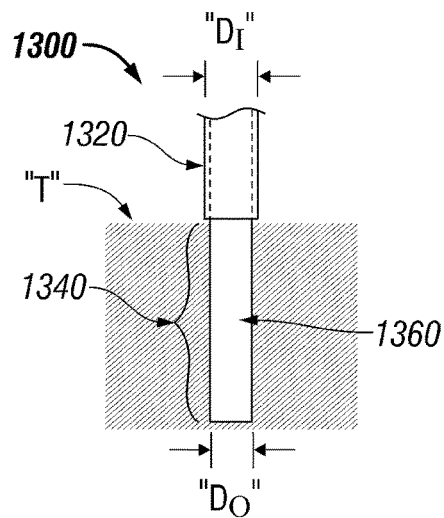

FIGS. 13A and 13B show a helical antenna assembly 1300 including a moveable shell 1320 located at a periphery of a sleeve member 1360 coaxially disposed with respect to sleeve member 1360. Shell 1320 is adapted to be slideably moveable along the periphery of the sleeve member 1360 between a first position, in which an outer diametrical wall of the sleeve member 1360 is entirely covered by the shell 1320 (see FIG. 13A), and a second position, in which at least a portion of the outer diametrical wall of the sleeve member 1360 is exposed (see FIG. 13B). In one embodiment, when the helical antenna assembly 1300 is operated in the normal mode, the shell 1320 is positioned in the second position. In another embodiment, when the helical antenna assembly 1300 is operated in the axial mode, the shell 1320 may be positioned in either the first or second position. Shell 1320 shown in FIGS. 13A and 13B is a substantially cylindrically-shaped structure having an inner diameter "$D_I$", which is larger than an outer diameter "$D_O$" of the sleeve member 1360. Shell 1320 may be slideably movable to various positions such that any portion of the helical radiating section of the helical antenna assembly 1300 may be exposed for radiating the tissue "T".

Figure 14:
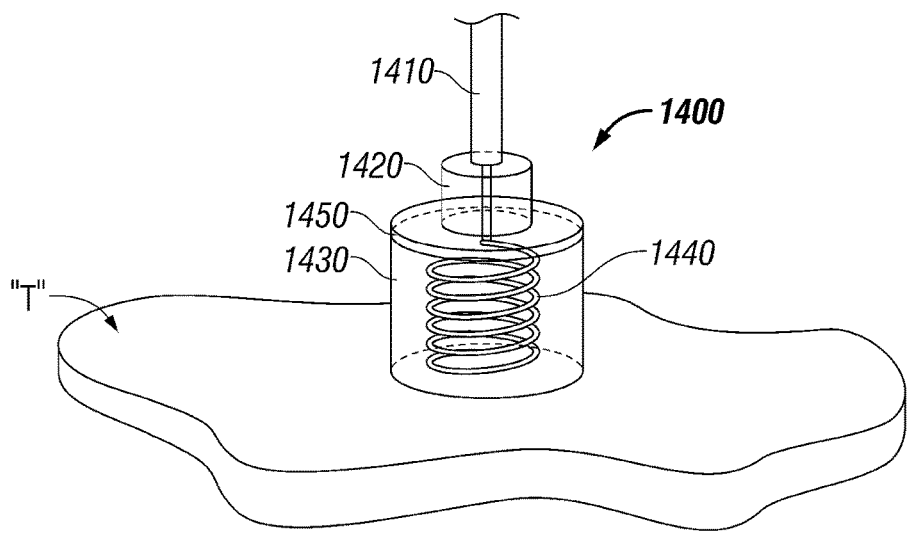
FIG. 14 is a perspective view of a helical antenna assembly, according to an embodiment of the present disclosure, positioned at the surface of the target tissue, prior to the operation of the helical antenna assembly.

FIG. 14 illustrates a helical antenna assembly 1400 that includes a helical antenna element 1440 disposed with a housing 1430 and backed by a conducting ground plane 1450 and a connector 1420, which is electrically coupled to the helical antenna element 1440 and a transmission line 1410. Helical antenna element 1440 may be configured as a dielectrically-loaded endfire helical antenna, which may be suitable for microwave ablation and/or for use to pre-coagulate tissue for microwave ablation assisted surgical resection. Helical antenna assembly 1400 may have an endfire radiation pattern similar to the endfire radiation pattern 310 of helical antenna assembly 200 shown in FIG. 3.

In one embodiment of helical antenna assembly 1400, a substantially cylindrically-shaped dielectric material is disposed within the housing 1430. The dielectric material within the housing 1430 may have a high permittivity such that the wavelength of the electromagnetic radiation, e.g., microwave radiation, transmitted by the helical antenna assembly 1400 is short enough to allow for a compact design. Helical antenna assembly 1400 may be configured in a variety of shapes and sizes depending on a particular surgical purpose or to accommodate a particular surgical need.

In one embodiment of helical antenna assembly 1400, the helical antenna element 1440 is formed of a shape-memory alloy, and the temperature of a fluid circulated around the helical antenna radiating section is varied to expand the circumference of the helical antenna radiating section and/or reduce the circumference of the helical antenna radiating section.

During various non-invasive procedures, the distal end of the helical antenna assembly 1400 may be placed in contact with the surface of a target tissue "T". In this instance, the endfire power would allow for targeting of surface tissue "T" placed in contact with the helical antenna assembly 1400. Layers of various metals and/or dielectric around the substantially cylindrically-shaped dielectric material disposed within the housing 1430 may be utilized to improve power delivery and directionality into surface tissue "T" and/or provide for a sterilizable device. A dielectric material, e.g., a dielectric gel, may be used between the distal end of the helical antenna assembly 1400 and the tissue "T", e.g., to improve coupling.

Figure 15:
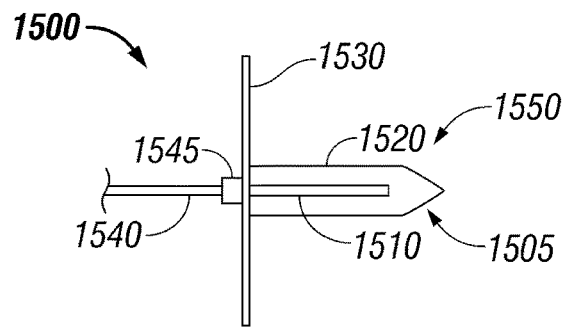
FIG. 15 is a schematic diagram of a monopole antenna assembly, according to an embodiment of the present disclosure.
Figure 16:
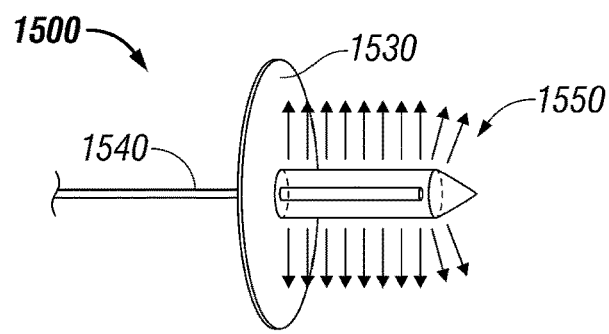
FIG. 16 is a perspective view of the monopole antenna assembly of FIG. 15 showing the transmission pattern.

FIG. 15 is a schematic diagram of a monopole antenna assembly 1500 that includes a monopole radiating section 1550 including a monopole antenna element 1510 surrounded by a dielectric material 1520 and backed by a ground plane 1530, a tip 1505, and a connector 1545, which is electrically coupled to the monopole antenna element 1510 and a transmission line 1540. Ground plane 1530 is configured to direct the electromagnetic radiation, e.g., microwave radiation, into the targeted tissue and may provide a boundary to define the resonant frequency of the monopole antenna assembly 1500. In one embodiment, dielectric material 1520 reduces the operating wavelength of the monopole radiating section 1550 and may buffer the microwave wavelength from tissue electrical property dynamics. FIG. 16 shows the transmission pattern of the monopole antenna assembly 1500.

Figure 17:
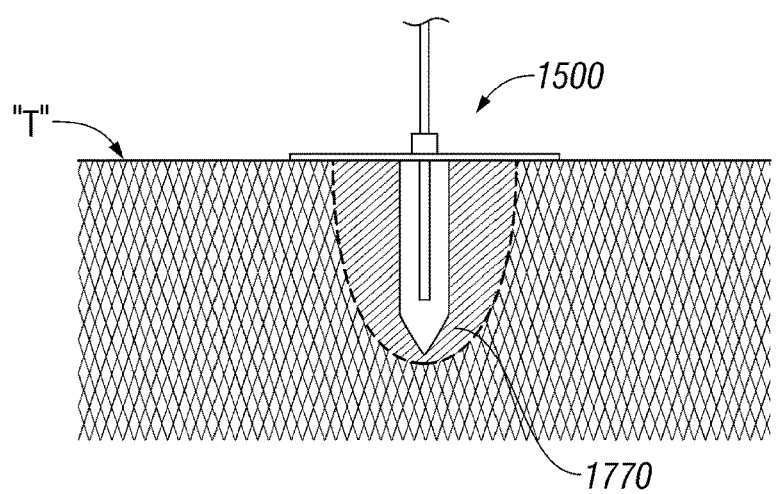
FIG. 17 is a schematic diagram of the monopole antenna assembly of FIGS. 15 and 16, positioned in the target surgical site, schematically illustrating thermal effects of microwave energy radiated into a portion of biological tissue.

FIG. 17 shows the monopole antenna assembly 1500 of FIGS. 15 and 16, positioned in the target surgical site, following the operation of the monopole antenna assembly 1500. FIG. 17 schematically illustrates thermal effects of microwave energy radiated into tissue "T", whereby a portion 1770 of the tissue "T" is abated around the monopole antenna assembly 1500.

Figure 18A:
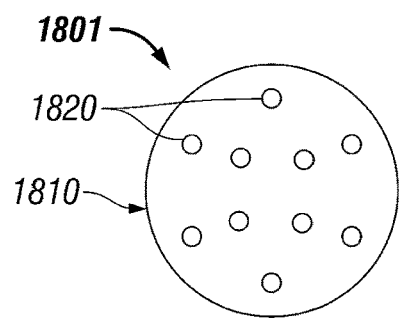
FIGS. 18A and 18B are schematic diagrams of electrosurgical devices including multiple monopole antenna assemblies, according to embodiments of the present disclosure.
Figure 18B:
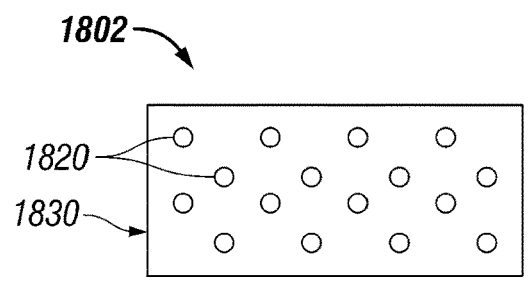

FIGS. 18A and 18B illustrate electrosurgical devices including multiple monopole antenna assemblies 1820. Components of the monopole antenna assemblies 1820 of FIGS. 18A and 18B may be similar to components of the monopole antenna assembly 1500 shown in FIGS. 15-17 (e.g., a monopole radiating section 1550 including the monopole antenna element 1510, dielectric material 1520, and tip 1505), and further description thereof is omitted in the interests of brevity. Various numbers and configurations of monopole antenna assemblies 1820 may utilize the same ground plane. For example, an electrosurgical device 1801 shown in FIG. 18A includes a substantially cylindrically-shaped housing 1810 configured with ten monopole antenna assemblies 1820 that are arranged substantially parallel to each other and which longitudinally extend from the distal end of the housing 1810. Referring to FIG. 18B, the electrosurgical device 1802 includes a substantially rectangular-shaped housing 1830 configured with sixteen monopole antenna assemblies 1820 that are arranged substantially parallel to each other in a longitudinally extending manner from the distal end of the housing 1830 and aligned in a pattern of rows and columns.

Figure 19:
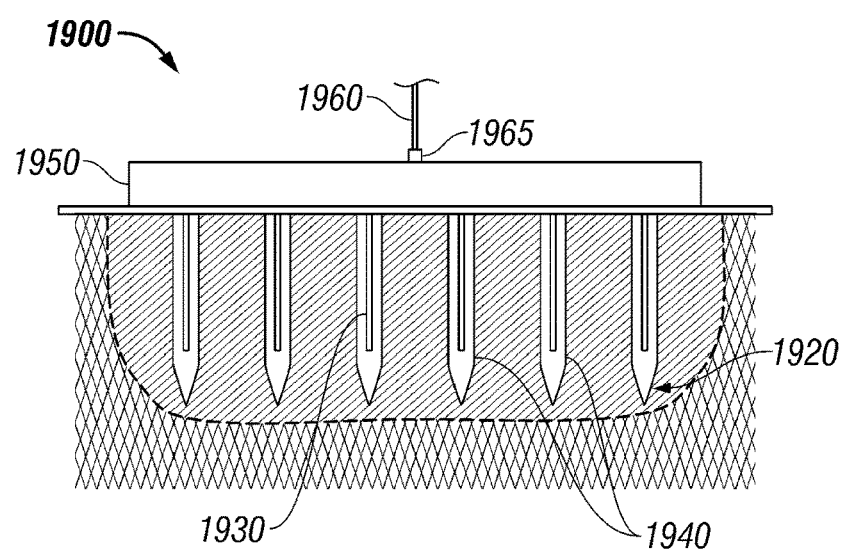
FIG. 19 is a schematic diagram of an electrosurgical device including multiple monopole antenna assemblies, according to an embodiment of the present disclosure, positioned in the target surgical site, schematically illustrating thermal effects of microwave energy radiated into a portion of biological tissue.

FIG. 19 shows an electrosurgical device 1900 that includes six monopole antenna assemblies 1920 that are commonly backed by a ground plane 1950. Each monopole antenna assembly 1920 includes a monopole antenna element 1930 surrounded by a dielectric material 1940. Ground plane 1950 is configured to direct the electromagnetic radiation, e.g., microwave radiation, into the target surgical site and may provide a boundary to define the resonant frequency of the respective monopole antenna assemblies 1920. The monopole antenna assemblies 1920 are inserted directly into tissue, through a lumen, such as, for example, a vein, needle or catheter, placed into the body during surgery by a clinician, or positioned in the body by other suitable methods.

Electrosurgical device 1900 also includes a power splitter 1950 that drives energy into each of the monopole antenna assemblies 1920, which is electrically coupled to each of the respective monopole antenna elements 1930. In one embodiment, power splitter 1950 is a microwave power splitter 1950.

Microwave power splitter 1950 may be implemented by any suitable power divider that provides substantially equal power split at all output ports. Microwave power splitter 1950 may be implemented by any suitable power divider that provides equal power split at all output ports while substantially maintaining phase and amplitude balance. For example, in one instance, the microwave power splitter 1950 implements using a 6-way power divider that provides equal power split at all output ports while maintaining a phase balance of <+/−10 degrees and amplitude balance of <1.5 dB.

Electrosurgical device 1900 also includes a connector 1965, which is electrically coupled to the power splitter 1950 and a transmission line 1960. Transmission line 1960 includes proximal and distal ends and may be suitable for transmission of microwave energy. The proximal end of the transmission line 1960 may be coupled to a microwave energy source (not shown), and the distal end thereof is in communication with the connector 1965 of the monopole antenna assembly 1900.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A helical antenna assembly for directing energy to a target volume of tissue, comprising:
   a helical antenna element;
   an outer shell coaxially disposed about the helical antenna element;
   a tip portion located at a distal end of the helical antenna element; and
   a conducting ground plane configured to direct energy into the target volume of tissue, wherein the helical antenna element extends outwardly from the conducting ground plane.

2. The helical antenna assembly of claim 1, further comprising a sleeve member coaxially disposed about the helical antenna element.

3. The helical antenna assembly of claim 2, wherein the sleeve member is formed of a dielectric material.

4. The helical antenna assembly of claim 2, wherein the sleeve member is formed of an inflatable element, a shape-memory alloy element, or a magneto-electrical actuated element.

5. The helical antenna assembly of claim 2, wherein the outer shell is configured to slideably move about the sleeve member in coaxial relation therewith.

6. The helical antenna assembly of claim 1, wherein the helical antenna element is formed of a shape-memory material.

7. The helical antenna assembly of claim 6, wherein the shape memory material is copper-zinc-aluminum-nickel, copper-aluminum-nickel, or nickel-titanium.

8. The helical antenna assembly of claim 1, wherein the outer shell is formed of a conductive material.

9. The helical antenna assembly of claim 1, further comprising a dielectric material disposed in an interior area defined by the helical antenna element.

10. The helical antenna assembly of claim 1, further comprising an inner shell disposed within the outer shell and about the helical antenna element, the inner shell extending an entire length of the helical antenna element.

11. The helical antenna assembly of claim 10, further comprising two longitudinally formed partitions that form a first channel and a second channel in a space between the outer shell and the inner shell.

12. The helical antenna assembly of claim 1, further comprising:
    a housing portion; and
    at least one further helical antenna element, wherein the helical antenna element and the at least one further helical antenna element are coupled to the housing portion and extend longitudinally from a distal end of the housing portion.

* * * * *